United States Patent [19]
Zoppetti et al.

[11] Patent Number: 6,162,797
[45] Date of Patent: Dec. 19, 2000

[54] DERIVATIVES OF K5 POLYSACCHARIDE HAVING HIGH ANTICOAGULANT ACTIVITY

[75] Inventors: Giorgio Zoppetti; Pasqua Oreste; Giovanni Cipolletti, all of Milan, Italy

[73] Assignee: Inalco S.p.A., Milan, Italy

[21] Appl. No.: 09/180,406

[22] PCT Filed: May 9, 1997

[86] PCT No.: PCT/EP97/02379

§ 371 Date: Nov. 6, 1998

§ 102(e) Date: Nov. 6, 1998

[87] PCT Pub. No.: WO97/43317

PCT Pub. Date: Nov. 20, 1997

[30] Foreign Application Priority Data

May 10, 1996 [IT] Italy ................................. MI96A0956

[51] Int. Cl.⁷ .................................................. A61K 31/715
[52] U.S. Cl. ................. 514/54; 514/56; 536/21; 536/53; 536/54; 536/55; 536/55.1; 536/55.2

[58] Field of Search ................... 514/53, 54, 56; 536/21, 53, 54, 55, 55.1, 55.2

[56] References Cited

U.S. PATENT DOCUMENTS 5,019,649 5/1991 Lormeau et al. .......................... 536/21
5,550,116 8/1996 Lormeau et al. .......................... 514/56

OTHER PUBLICATIONS

Carbohydrate Letters, vol. 1, pp. 107–114, 1994.
TIBS 13, Jun. 1998, pp. 221–225.

*Primary Examiner*—James O. Wilson
*Attorney, Agent, or Firm*—Hedman, Gibson & Costigan, P.C.

[57] ABSTRACT

Derivatives of the K5 polysaccharide having anticoagulant activity higher than heparin, obtained by a process including the steps of reacting: with an organic base a solution of K5 polysaccharide N-deacetylated, N-sulfated and epimerized at least to an iduronic acid content of 50% treating with a sulfating agent to obtain the N-resulfation of the possible N-desulfated groups.

14 Claims, 2 Drawing Sheets

DERIVATIVES OF K5 POLYSACCHARIDE HAVING HIGH ANTICOAGULANT ACTIVITY

The present application is the national stage filing of and claims priority to International Application No. PCT/EP97/02379, filed May 9, 1997 and Italian Application Serial No. MI96A000956.

PRIOR ART

It is known that the product mainly used in anticoagulant therapy is the heparin obtained by extraction from animal organs. However the production of heparin from animal organs employs great amounts of solvents and chemical agents involving disposal and therefore potential environmental pollution problems. Moreover the final product may contain residues of biological substances normally or exceptionally present in the animal tissues as viruses or prions. O-sulfation processes carried out on derivatives of the K5 polysaccharide (B. Casu et al., Carbohydrate Letters, 1, 107–114 (1994)) are also known.

The publications by B. Casu et al. refer to O-sulfations carried out on K5 which result in products showing an anticoagulant strength lower then the commercial heparin.

This is also due to the fact that the entirety of uronic acids is represented by glucuronic acids. The glucuronic acid gives to the polysaccharidic chain a lower flexibility towards the target proteins such as for example the antithrombin III and then a lower anticoagulant activity (B. Casu, M. Petitou, M. Provasoli and P. Sinay (1988). Conformational flexibility: a new concept for explaining binding and biological properties of iduronic acid containing glycosaminoglycans. Trends Biochem. Sci. 13, 221–225).

SUMMARY

Now a process for the preparation of new derivatives of the K5 polysaccharide which allow to overcome the drawbacks of the prior art has been found.

Said process includes the following steps:

a) the K5 polysaccharide is N-deacetilated;

b) the product obtained in the step a) is N-sulfated;

c) the product obtained in the step b) is epimerized to the achievement of at least 50% of iduronic acid with respect to the total of uronic acids, and it is characterized in that the product obtained in the step c) is further treated according to the following steps:

d) the product obtained in the step c) is dissolved in water and percolated through a column containing a cation exchange resin;

e) the solution obtained in the step d) is reacted with an organic base;

f) the solution obtained in the step e) is freeze-dried and the obtained product is redissolved in an organic solvent and treated with a sulfating agent to obtain the O-sulfation;

g) the product obtained in the step f) is precipitated, redissolved in distilled water and dialyzed against distilled water;

h) If it is necessary, the product obtained in the step g) is treated with a sulfating agent in order to obtain the N-resulfation of the in case N-desulfated groups.

Optionally the product obtained after the step h) is depolymerized by controlled nitrous acid degradation according to known technology (i.e. U.S. Pat. No. 5,019,649).

The products according to the present invention have, beside new characteristics, a high anticoagulant activity, greater than the anticoagulant activity of the heparin obtained by extraction from animal tissues.

DETAILED DESCRIPTION OF THE INVENTION

Figure 1:
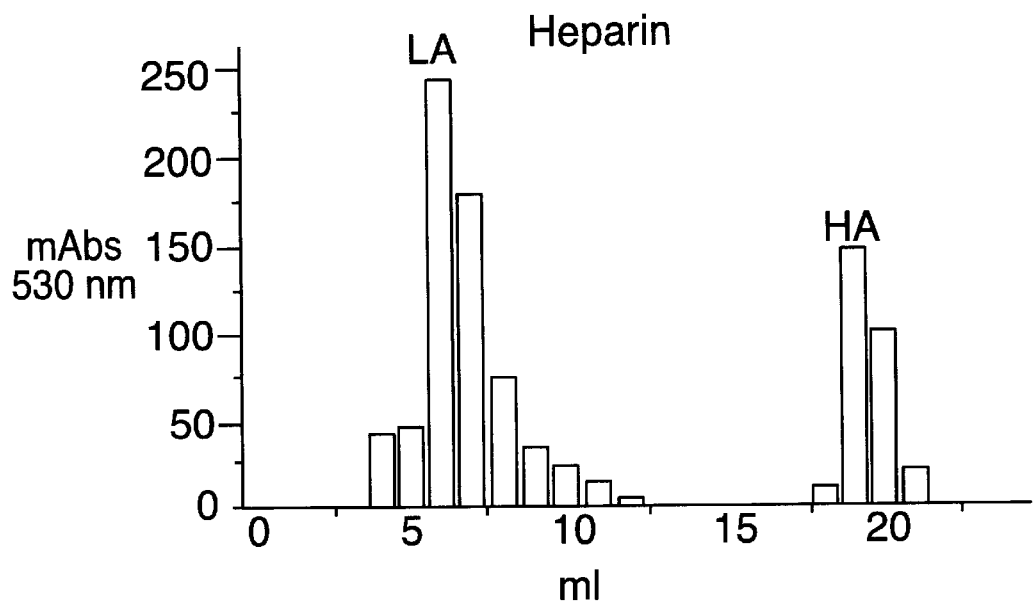
FIG. 1 represents the data relative to the affinity of heparin for antithrombin III.

The characteristics and the advantages of the derivatives of the K5 polysaccharide and the relative preparation process according to the present invention will be mostly pointed out during the following detailed description. The starting material for the achievement of said derivatives is the K5 polysaccharide obtained from *E. Coli* as described by M. Manzoni, S. Bergomi and V. Cavazzoni (Journal of Bioactive and Compatible Polymers. Vol. VIII, July 1993, 251–257). The K5 polysaccharide is first of all treated as in the following steps:

a) the K5 polysaccharide is N-deacetilated;

b) the product obtained in the step a) is N-sulfated in order to obtain N-sulfated K5 from 25 to 100%;

c) the product obtained in the step b) is epimerized with D-glucuronyl L-iduronyl C5 epimerase extracted from bovine liver in order to obtain a product having a L-iduronic acid content from 50 to 90% with respect to the total of the uronic acids.

The N-deacetilation of the step a) is carried out by treatment with a hydrazine and hydrazine sulfate mixture or in an alkaline environment with sodium hydroxide or potassium hydroxide. Subsequently the N-sulfation of the step b) is carried out by treatment with triethylamine-sulfur trioxide or with trimethylamine-sulfur trioxide. The N-deacetilation and N-sulfation reactions are carried out according to the known techniques, for example according to the Patent WO 92/17507.

The N-sulfated product is then submitted to the epimerization reaction of the step c) in order to convert the glucuronic acid in iduronic acid. The epimerization is carried out present the D-glucuronyl-L-iduronyl-C5-epimerase enzyme (hereinafter simply denoted with C5-epimerase) extracted from bovine liver and purified by the method described by A. Malmstrom in J. B. C. 255, 3878–3883 (1980). The reaction medium is a buffer solution at pH 7.4 for example consisting of HEPES 0.04 M or TRIS 0.05 M, potassium chloride, EDTA and TRITON X-100 and added with one or more additives selected from the group consisting of glycol, glycerol, polyvinylpyrrolidone, particularly polyvinylpyrrolidone having a molecular weight from 15,000 to 90,000, glycol and lecithin in such an amount to increase the viscosity of the buffer solution to values ranging from 1.1 to 3 centistokes. In particular the reaction medium is prepared starting from a suitable buffer solution having pH 7.4; such as for example HEPES 0.04 M, KCl 0.4 M and EDTA 0.06 M and to 25 ml of this solution from 100 to 1000 μl of TRITON X-100, from 0.5 ml to 60 ml of additive and distilled water to 100 ml are added. The polysaccharide to submit to epimerization is added to said reaction medium in amounts from 5 to 1000 mg per 100 ml obtaining the solution A. The C-5 epimerase is 20 dissolved separately in the same reaction medium above mentioned in amounts from 21 to 2000 μg per 100 ml obtaining the solution B. The solution B is added to the solution A in such a proportion to obtain a C-5 epimerase content from 1.5 to 15,000 μg per 100 ml of mixture to submit to epimerization.

The mixture is homogenized by stirring and heated at a temperature ranging from 30 to 40° C. in a constant-temperature chamber for a time ranging from 90 minutes to 15 hours.

The reaction in stopped heating the mixture at 100° C. for 5 minutes. The product is purified through a DEAE-Sephacel column using $(NH_4)HCO_3$ or NaCl 0.05 M as buffer and eluting the product with buffer $(NH_4)HCO_3$ or NaCl 2 M.

The gathered fractions are desalted by Sephadex G-15 column, the fraction containing the product is freeze-dried and the product is analyzed by 1H-NMR. From the 1H-NMR spectrum the D-glucuronic acid and the L-iduronic acid content is computed.

The obtained product may be redissolved in the solution A and treated again with the solution B obtaining, with further epimerization treatments, an increase of the L-iduronic acid content.

The product obtained from the step c) as described above is further treated as described in the following steps, which characterize the present invention:

d) the product obtained in the step c) is dissolved in water and percolated through a column containing a cation exchange resin such as for example Amberlite IR 120 $H^+$ (Rohm and Haas) which is subsequently washed with distilled water.

The pH of the obtained solution ranges from 0.5 to 1.5;

e) the solution obtained in the step d) is treated with an organic base preferably selected from the group consisting of trimethylamine, triethylamine and tributylamine, dissolved in an organic solvent such as for example alcohol. The organic base amount added is such to obtain a solution pH ranging from 6.5 to 7.0. The organic base excess is removed by treatment with diethyl ether;

f) the solution obtained in the step e) is freeze-dried and the obtained product is redissolved in an organic solvent at room temperature and treated with a sulfating agent at a temperature ranging from −5 to 60° C. for a time period ranging from 10 to 24 hours, in order to obtain the O-sulfation.

Said organic solvent is preferably the anhydrous dimethylformamide and said sulfating agent is preferably selected from the group consisting of pyridine sulphur trioxide, trimethylamine sulphur trioxide, triethylamine sulphur trioxide, tripropylamine sulphur trioxide and tributyl amine sulphur trioxide;

g) the solution obtained in the step f) is diluted with an equal volume of water, a solution of NaOH at 4% is added to reach a pH equal to 9 and the product is precipitated by addition of 4 volumes of alcohol saturated by sodium acetate and maintaining the temperature from 3 to 5° C. for 10–15 hours. The obtained precipitate is dissolved in distilled water and dialyzed against distilled water in a 1,000 cut-off dialysis membrane for 3 days with extra-dialysis change every day;

h) if it is necessary, the solution obtained in the step g) is added with sodium bicarbonate to pH 9, it is heated at a temperature raging from 50 to 60° C. and a sulfating agent selected from the group pointed out in the step f) is added in order to obtain the N-resulfation of the groups in case desulfated during the treatment. This reaction is carried out under stirring for a period of time ranging from 5 to 10 hours, at a temperature ranging from 50 to 60° C.

At the end the solution is desalted by a 3500 D dialysis against decreasing solutions of NaCl for S days and the product is freeze-dried.

Optionally the product obtained after the step h) is depolymerized by controlled nitrous acid degradation according to known technology (i.e. U.S. Pat. No. 5,019,649).

K5 polysaccharides derivatives having new characteristics and an anticoagulant activity greater than the heparin one obtained by the extraction from animal tissues are obtained by the described process. The derivatives according to the present invention contain from 40 to 100% of chains affine for the Antithrombin III, computed according to the method described by M. Hook et al. (FEBS letters, 66, 1976, 90–93), while the heparin contains only 30% of chains affine for the Antithrombin III and this explains its greater anticoagulant activity. In the following Table 1 the values of the chemical analysis and the anticoagulant activity in vitro of the derivatives according to the invention (A) in comparison with the commercial heparin (B) are reported.

TABLE 1

|  | (A) | (B) |
| --- | --- | --- |
| Sulfates/carboxyls ratio | 2.2–2.5 | 1.9–2.4 |
| N-sulfates content | 70%–100% | 86%–91% |
| 6-O-sulfates content | 70%–90% | 64%–89% |
| 2-O-sulfates content | 50%–60% | 71%–78% |
| 3-O-sulfates content | 5%–10% | 0.5%–2.0% |
| Chains affine for the Antithrombin III | 40%–100% | 28–35 |
| Anti-Xa | 500–600 | 145–197 |
| APTT | 250–320 | 145–187 |

The sulfates/carboxyls ratio has been determined by the conductimetric method according to B. Casu et al. (Carbohyd. Res. 39.168 (1975)) while the sulfates distribution has been determined by nuclear magnetic resonance according to B. Casu et al. (Arzneim. Forsch./Drug Res. 33(I), 1, 135–142–1983).

The 3-O-sulfates content has been determined by the method described by B. Casu et al. (Biochem J. 197, 1981, 599–609).

The anticoagulant activity has been measured as APTT according to L. Andersson et al. (Thrombosis Res. 9, 575–1976), and as Anti Xa according to D. P. Thomas et al. (Thrombosis and Haemostasis 45, 214–1981).

Thanks to their characteristics the derivatives according to the present invention may be used for the preparation of pharmaceutical compositions suitable to the anticoagulant treatment in the human therapy.

Said compositions contain efficacious amounts of said derivatives in combination with pharmacologically acceptable excipients or diluents. The posology for the human therapy is from 30 to 200 mg per day.

The derivatives according to the present invention also exhibit with respect to heparin the great advantage to be viruses and prions free and the production process has the advantage not to give polluting effluents.

EXAMPLE 1

10 mg of 100% N-sulfated and 70% epimerized (that is containing 70% of iduronic acid with respect to the uronic acids total) K5 have been dissolved in 2 ml of water and put into an Amberlite IR 120$H^+$ column at room temperature.

The column has been washed with 10 ml of water. The eluate plus the washing liquid had a pH equal to 1.5. The solution has been added with tributylamine to pH 5.5 using a solution of tributylamine at 10% in ethanol. The excess of tributylamine not bound to the polysaccharide has been removed by treatment with diethyl ether. The solution has been finally freeze-dried.

Then the product has been redissolved in 3.2 ml of anhydrous dimethylformamide at room temperature and 3 ml of anhydrous dimethylformamide containing 0.153 g of piridine-sulphur trioxide have been added. The obtained solution has been kept at room temperature for 6 hours and then diluted with an equal volume of water. The pH has been finally set to 9 with NaOH at 4% and the product has been precipitated with 4 volumes of ethanol saturated with sodium acetate keeping the solution at 4° C. overnight. The obtained precipitate has been dissolved in 10 ml of distilled water and dialyzed against distilled water in a 1,000 cut-off dialysis membrane for 3 days with extra-dialysis change every day.

The obtained sample has been submitted to N-resulfation. The pH has been set to 9 with the addition of solid sodium bicarbonate, the temperature has been raised to 55° C. and 6.5 ml of trimethylamine-sulphur trioxide have been added under stirring. The solution has been kept at 55° C. for 1 hour, further 6.5 ml of trimethylamine-sulphur trioxide have then been added and the reaction carried on for additional 5 hours. The sample has been desalted by 3500 D dialysis against solutions having decreasing NaCl concentration for 5 days (0.5 M the first day, 0.2 M the second day, 0.1 M the third day and water the fourth and the fifth day). The product has been finally freeze-dried.

The obtained product exhibits a sulfates/carboxyls ratio equal to 2.5, 100% N-sulfates content, 80% 6-O-sulfates content, 60% 2-O sulfates, 10% 3-O sulfates, a fraction affine to the AT III equal to 100% and the following in vitro anticoagulant activities:

| Anti-Xa | 600 U/mg |
|---|---|
| APTT | 310 U/mg |

EXAMPLE 2

10 mg of 90% N-sulfated and 60% epimerized K5 have been treated as in the Example 1 with the difference that, after the N-resulfation, the product has been treated at a temperature equal to 40° C. with 10 ml of anhydrous dimethylformamide containing 0.51 g of pyridine-sulfur trioxide added under stirring.

After 2 hours further 10 ml of anhydrous dimethylformamide containing 0.51 g of pyridine-sulfur trioxide have been added and the reaction has been continued for additional 10 hours.

The product has been desalted as in the Example 1.

The obtained product exhibits a sulfates/carboxyls ratio equal to 2.4, 90% N-sulfates content, 100% 6-O sulfates content, 40% 2-O sulfates, 7% 3-O sulfates, a fraction affine to the AT III equal to 85% and the following in vitro anticoagulant activities:

| Anti-Xa | 550 U/mg |
|---|---|
| APTT | 290 U/mg |

EXAMPLE 3

10 mg of 80% N-sulfated and 55% epimerized K5 have been treated as in the Example 1 with the difference that, after the N-resulfation, the product has been treated at a temperature equal to 65° C. with 10 ml of anhydrous dimethylformamide containing 0.51 g of pyridine-sulfur trioxide added under stirring.

After 2 hours further 10 ml of anhydrous dimethylformamide containing 0.51 g of pyridine-sulfur trioxide have then been added and the reaction has been continued for additional 5 hours.

The product has been desalted as in the Example 1.

The obtained product exhibits a sulfates/carboxyls ratio equal to 2.5, 80% N-sulfates content, 100% 6-O sulfates content, 65% 2-O sulfates, 5% 3-O sulfates, a fraction affine to the AT III equal to 70% and the following in vitro anticoagulant activities:

| Anti-Xa | 450 U/mg |
|---|---|
| APTT | 270 U/mg |

In the Table 2 the data relative to the characteristics of the products of the Examples have been summarized, from which one may notice particularly that the anticoagulant activity decreases with the decrease of the iduronic acid content.

EXAMPLE 4

10 mg of the product obtained in the Example 3 are dissolved in 10 ml of distilled water and added with 0.34 mg of sodium nitrite.

Immediately the pH is brought to 2.5 with hydrochloric acid 0.01 N. After 40 minutes the solution is neutralised with sodium hydroxide and the compound is recovered by precipitation with 3 volumes of ethanol and dried in a vacuum oven.

The compound obtained shows a sulphate/carboxyl ration of 2.2, N-sulphate content of 70%, 6-O sulphate content of 65%, 2-O sulphate content of 60%, 3-O sulphate content of 4%, an ATIII high activity fraction of 40% and the following in vitro anticoagulant activities:

| Anti-Xa | 200 U/mg |
|---|---|
| APTT | 70 U/mg |

TABLE 2

|  | Example 1 | Example 2 | Example 3 | Example 4 |
|---|---|---|---|---|
| Sulfates/carboxyls ratio | 2.5 | 2.3 | 2.4 | 2.2 |
| Mean molecular weight | 14,000 | 14,000 | 14,000 | 5,000 |
| N-sulfates | 100% | 90% | 80% | 70% |
| 6-O sulfates | 80% | 90% | 70% | 65% |
| 2-O sulfates | 60% | 50% | 60% | 60% |

TABLE 2-continued

|  | Example 1 | Example 2 | Example 3 | Example 4 |
|---|---|---|---|---|
| 3-O sulfates | 10% | 7% | 5% | 4% |
| Iduronic Acid | 70% | 60% | 55% | 55% |
| Fraction having high affinity for AT III | 100% | 85% | 70% | 40% |
| Anti-Xa | 600 U/mg | 550 U/mg | 500 U/mg | 200 U/mg |
| APTT | 310 U/mg | 290 U/mg | 250 U/mg | 70 U/mg |

Figure 2:
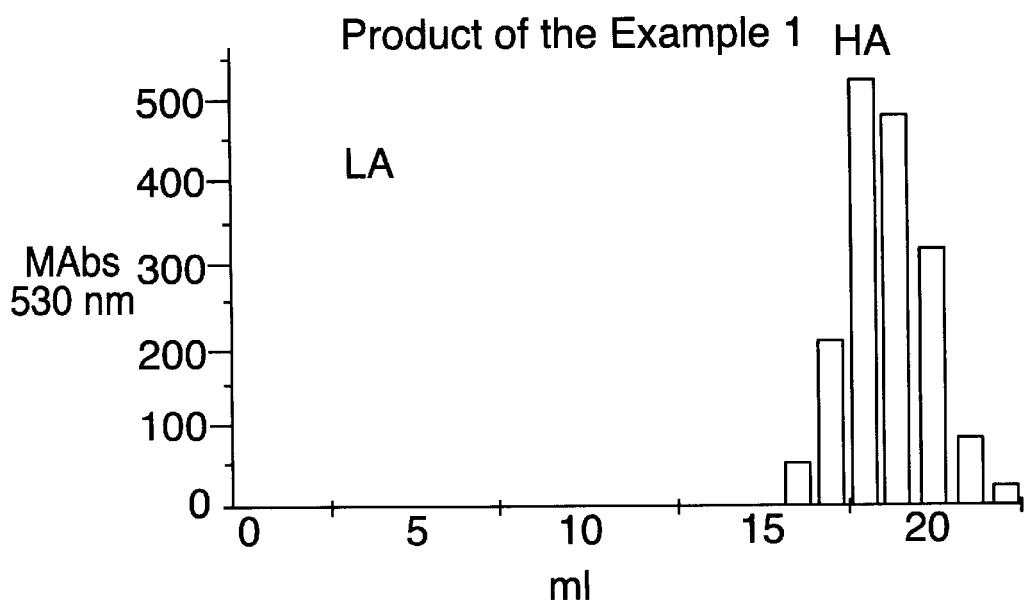
FIG. 2 represents the data relative to the affinity of the derivative of Example 1 for antithrombin III.
Figure 3:
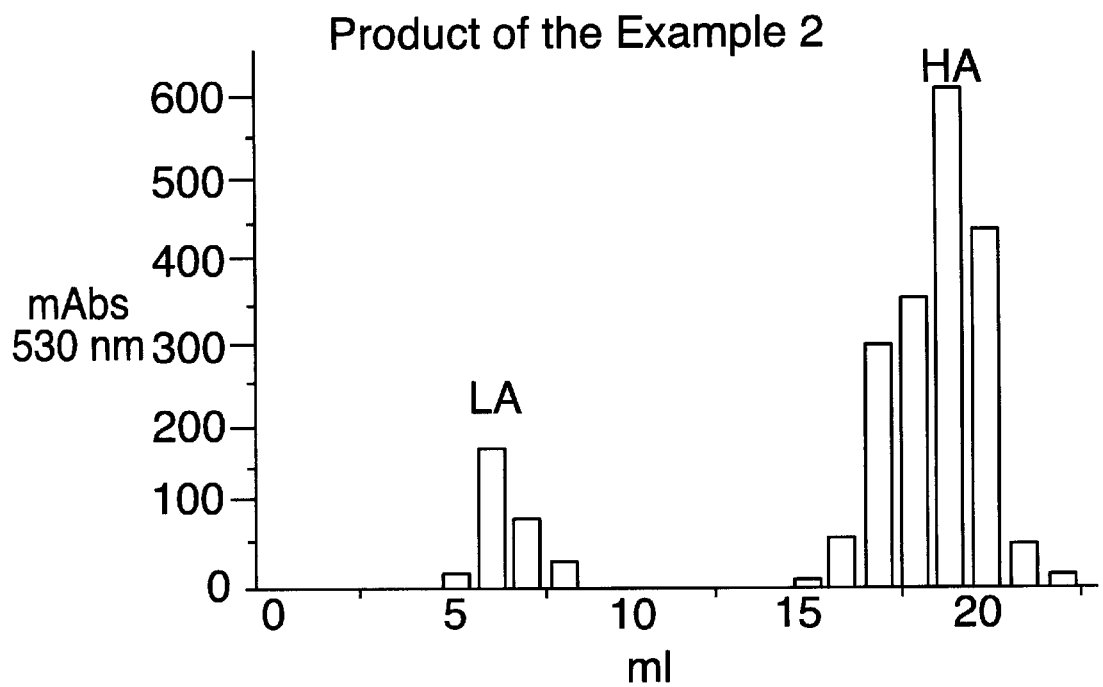
FIG. 3 represents the data relative to the affinity of the derivative of Example 1 for antithrombin III.
Figure 4:
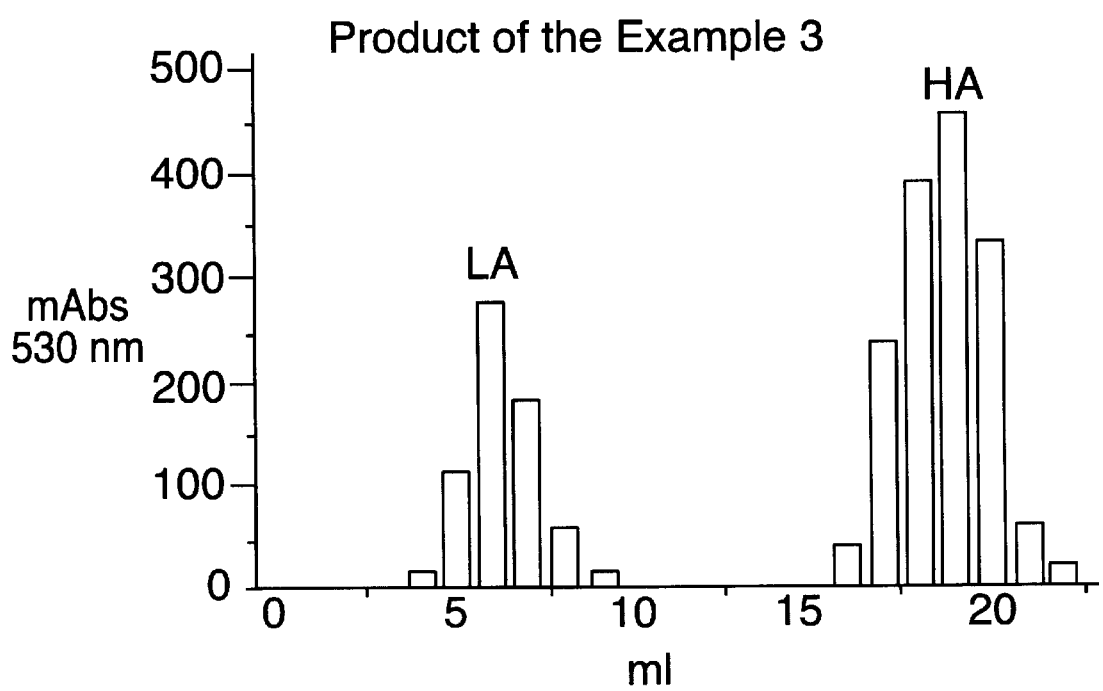
FIG. 4 represents the data relative to the affinity of the derivative of Example 3 for antithrombin III.

In the FIGS. 2, 3, and 4 the data relative to the affinity for the antithrombin III for the products of the Examples 1, 2 and 3 are reported, while in the FIG. 1 are reported, by comparison, the same data for the heparin.

In said Figures:

mAbs 530 nm means milliabsorbance determined at 530 nm;

LA means fraction having low affinity for the antithrombin III;

HA means fraction having high affinity for the antithrombin III;

These data confirm what has been reported as commentary of the Table 2.

What is claimed is:

1. Process for the preparation of derivatives of the K5 polysaccharide having anticoagulant activity higher than heparin, wherein:
   a) the K5 polysaccharide, N-deacetylated, N-sulfated and epimerized at least to a iduronic acid content equal to 50%, with respect to the total of uronic acids, is dissolved in water and percolated through a column containing a cation exchange resin;
   b) the solution obtained in the step a) is reacted with an organic base;
   c) the-solution of the step b) is freeze-dried and the obtained product is redissolved in an organic solvent and treated with a sulfating agent to obtain the O-sulfation;
   d) the product obtained in the step c) is precipitated, redissolved in distilled water and dialyzed against distilled water;
   e) the product obtained in step d) is if necessary treated with a sulfating agent in order to obtain the N-resulfation of any N-desulfated groups.

2. Process as claimed in claim 1, characterized in that the solution obtained in step a) has a pH ranging from 0.5 to 1.5.

3. Process as claimed in claim 1, characterized in that said organic base used in step b) is selected from the group consisting of trimethylamine, triethylamine and tributylamine.

4. Process as claimed in claim 1, characterized in that the amount of organic base used in step b) is such to obtain a solution pH ranging from 6.5 to 7.0.

5. Process as claimed in claim 1, characterized in that said organic solvent used in step c) consists of anhydrous dimethylformamide.

6. Process as claimed in claim 1, characterized in that said sulfating agent used in step c) is selected from the group consisting of pyridine-sulfur trioxide, trimethylamine-sulfur trioxide, triethylamine-sulfur trioxide, tripropylamine-sulfur trioxide and tributylamine-sulfur trioxide.

7. Process as claimed in claim 1, characterized in that said treatment with a sulfating agent of step c) is carried out at a temperature ranging from −5 to 60° C. for a time period ranging from 10 to 24 hours.

8. Process as claimed in claim 1, characterized in that said precipitation of step d) is carried out by diluting the solution obtained in step c) with an equal volume of water, adjusting the pH to 9, adding 4 volumes of alcohol; saturated with sodium acetate and keeping the temperature in the range of 3 to 5° C. for a time period ranging from 10 to 15 hours.

9. Process as claimed in claim 1, characterized in that said sulfating agent used in step e) is selected from the group consisting of pyridine-sulfur trioxide, trimethyl-sulfur trioxide, triethylamine-sulfur trioxide, tripropylamine-sulfur trioxide and tributylamine-sulfur trioxide.

10. Process as claimed in claim 2, characterized in that said N-resulfation reaction of step e) is carried out at pH 0, at a temperature ranging from 50 to 60° C. for a time period ranging from 5 to 10 hours.

11. Derivatives of the K5 polysaccharide epimerized at least to 50% of iduronic acid with respect to the total of uronic acid, having:

| sulfate/carboxyl ratio | 2.2–2.5 |
|---|---|
| N-sulfates content | 70–100% |
| 6-O-sulfates content | 70–90% |
| 2-O-sulfates content | 50–60% |
| 3-O-sulfates content | 5–10% |
| Chains affine for the Antithrombin III | 40–100% |
| Anti - Xa | 500–600 |
| APTT | 250–320. |

12. Pharmaceutical compositions suitable for anticoagulant treatment of humans, said compositions consisting of effective amounts of derivatives of the K5 polysaccharide as claimed in claim 11, in combination with pharmacologically acceptable excipients or diluents.

13. Therapeutic method for anticoagulant treatment of humans, said method consisting in the administration of a derivative of the K5 polysaccharide as claimed in claim 11, in amounts of 30 to 200 mg per day.

14. Process as defined in claim 1 wherein the product obtained in step e) is depolymerized by controlled nitrous oxide degradation.

* * * * *